United States Patent [19]

Yutori et al.

[11] Patent Number: 5,306,252
[45] Date of Patent: Apr. 26, 1994

[54] CATHETER GUIDE WIRE AND CATHETER

[75] Inventors: Toshiaki Yutori; Masahiko Uchimura; Yoshinobu Mizukawa, all of Kobe, Japan

[73] Assignee: Kabushiki Kaisha Kobe Seiko Sho, Kobe, Japan

[21] Appl. No.: 912,765

[22] Filed: Jul. 13, 1992

[30] Foreign Application Priority Data

Jul. 18, 1991 [JP] Japan ............................ 3-203286
May 19, 1992 [JP] Japan ............................ 4-152852

[51] Int. Cl.$^5$ ..................... A61M 25/01; A61B 5/00
[52] U.S. Cl. ..................... 604/164; 604/282; 128/772; 138/130; 267/168
[58] Field of Search ............... 128/772, 657; 604/282, 604/264, 164; 464/58; 138/130; 74/502.5; 267/168

[56] References Cited

U.S. PATENT DOCUMENTS

| 4,613,385 | 9/1986 | Thomas et al. | 148/599 |
| 4,925,445 | 5/1990 | Sakamoto et al. | 604/95 |
| 5,107,852 | 4/1992 | Davidson et al. | 128/772 |
| 5,165,421 | 11/1992 | Fleischhacker | 128/772 |

FOREIGN PATENT DOCUMENTS 0200430 11/1986 European Pat. Off. .
0386921 9/1990 European Pat. Off. .

Primary Examiner—Randall L. Green
Assistant Examiner—D. Willse
Attorney, Agent, or Firm—Oblon, Spivak, McClelland, Maier & Neustadt

[57] ABSTRACT

A catheter guide wire which, despite its reduced diameter, exhibits improved strength and resistance to corrosion by body fluids and medicines. The catheter guide wire 10 is composed of a stainless steel core wire 11, a winding of a low carbon duplex structure steel wire 13 having a diameter smaller than 30 μm and a tensile strength higher than 300 kgf/mm², said winding covering the core wire such that tiers of the low carbon duplex structure steel wire run obliquely to the axis of the core wire 11 and have turns crossing each other, and a polyester resin film 15, thinner than 3 μm, covering the low carbon duplex structure steel wire 13. The catheter is composed of a resin inner tube and a low carbon duplex structure steel wire 13 covered with a polyester resin film 15, which runs around the resin inner tube obliquely to the axis and crosses each other.

4 Claims, 4 Drawing Sheets

CATHETER GUIDE WIRE AND CATHETER

BACKGROUND OF THE INVENTION

1. Field of the Invention

The present invention relates to a catheter to be used for diagnosis and medical treatment and also to a guide wire to keep the catheter approximately straight. More particularly, the present invention relates to a catheter and a catheter guide wire which have improved resistance to corrosion by body fluids and drugs. The catheter has such an entirely new structure that the forward end thereof is provided with a heating part which permits the accurate temperature control of the medicine to be injected hot.

2. Description of the Prior Art

Much attention is now focused on the new method of diagnosis and medical treatment which involves the insertion of a tubular catheter into the heart, lung, stomach, or blood vessel for the extraction of body fluids or blood or for the infusion of blood or medicine. The catheter for this purpose has an L-shaped tip and is flexible so that it can be inserted into complicatedly bent blood vessels. To facilitate insertion into the body, the catheter is kept approximately straight by the aid of a guide wire inserted into it. This guide wire should have the following characteristic properties.

Sufficient flexibility to permit the catheter to bend easily along the blood vessels.

Sufficient strength to keep the tip of the catheter approximately straight.

Small outside diameter to permit its insertion into the thin catheter.

Good resistance to corrosion by body fluids and blood.

The conventional guide wire which meets these requirements is composed of a stainless steel core wire and two layers of windings of extremely thin stainless steel wire (about 30 μm in dia.) on the core wire, with the inner windings being oblique to the axis of the core wire and the outer windings crossing the inner windings.

What is required of the above-mentioned catheter for diagnosis and medical treatment are:

Small outside diameter and large inside diameter.

Good flexibility.

Good buckling resistance (which prevents the catheter from being collapsed when it is bent).

Ability to transmit torque (for manipulation) to its tip.

The conventional catheter to meet these requirements is made from a tube of fluoroplastic (such as Teflon).

The above-mentioned catheter has recently found a new use for the remedy of obstructive jaundice induced by liver cancer. In other words, the catheter is used to inject blood or medicine (such as anticancer drug) hot directly into the affected part. The conventional method involves the heating of medicine by a warmer coil and the injection of the heated medicine through the catheter.

For the effective diagnosis and medical treatment, it is necessary that the catheter be brought as close to the affected part as possible. This requires the catheter to have a smaller outside diameter and the guide wire to have a smaller diameter accordingly. A conceivable way to meet this requirement is by further reduction in the diameter of the stainless steel wire. Mere reduction in diameter, however, results in insufficient strength, making it difficult for the guide wire to keep the catheter straight, which leads to the inconvenient manipulation of the catheter. There is a limit to reducing the diameter of the stainless steel wire.

One possible way of reducing the outside diameter of the conventional catheter is by the reduction of the wall thickness of the inserting part, because it is necessary to secure a certain inside diameter necessary for blood extraction or medicine injection. A problem associated with reducing the wall thickness is that the catheter is liable to collapse and to become poor in torque transmission ability. This is another factor that limits the reduction of the diameter.

It is expected that the reduction in diameter of the guide wire and catheter will be achieved with the low carbon duplex structure steel wire which had previously been proposed by the present inventors. It is produced from a wire rod, 3.0–6.0 mm in diameter, composed of C: 0.01–0.50%, Si: 3.0% or less, Mn: 5.0% or less, with the remainder being Fe and inevitable impurities (by weight), by the steps of primary heat treatment, primary cold drawing, secondary heat treatment, and secondary cold drawing. The thus produced steel wire has a diameter smaller than 30 μm and a tensile strength higher than 300 kgf/mm². In other words, it is stronger and tougher than stainless steel wire for the same diameter. Therefore, if the low carbon duplex structure steel wire is used as a reinforcement for the guide wire and catheter, it would be possible to reduce the diameter while meeting the above-mentioned requirements.

Unfortunately, the low carbon duplex structure steel wire has a disadvantage that it immediately rusts upon direct contact with body fluids, medicine, or air because it is extremely thin. Therefore, it should be given corrosion resistance.

According to the conventional practice it is necessary to heat medicine or blood using a warmer coil before it is injected hot through a catheter. The heated medicine or blood decreases in temperature when it reaches the affected part and the actual temperature is not known. In other words, the method for injecting blood or medicine hot through the conventional catheter poses a problem associated with inaccurate temperature control.

SUMMARY OF THE INVENTION

The present invention was completed to cope with the above-mentioned situation. It is an object of the present invention to provide a catheter and a catheter guide wire which meet the requirements for reduction in diameter and have good resistance to corrosion by body fluids. It is another object of the present invention to provide a catheter that permits accurate temperature control in the case where medicine is injected hot.

DESCRIPTION OF THE PREFERRED EMBODIMENTS

Figure 1A:
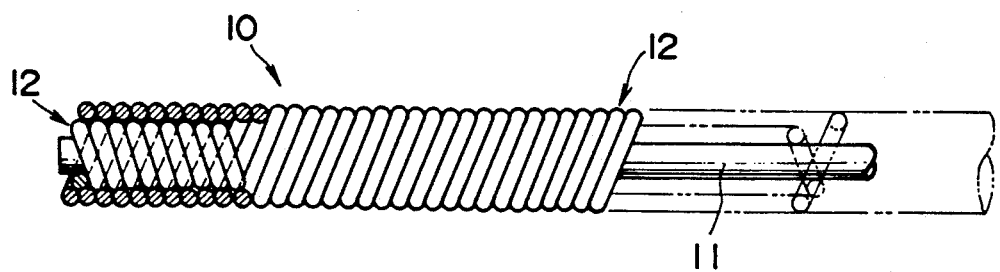
FIGS. 1(*a*) and 1(*b*) are views illustrating the catheter guide wire in the first embodiment pertaining to the first and second aspects of the present invention.

The first aspect of the present invention resides in a guide wire to keep a tubular catheter approximately straight, said guide wire comprising a core wire, a winding of a low carbon duplex structure steel wire having a diameter smaller than 30 μm and a tensile strength higher than 300 kgf/mm², said winding having two tiers covering the core wire such that the turns of the low carbon duplex structure steel wire run obliquely to the axis of the core wire and cross each other, and a polyester resin film covering the low carbon duplex structure steel wire.

The second aspect of the present invention resides in a guide wire as defined in the first aspect, wherein the polyester resin film has a thickness smaller than 5 μm.

The third aspect of the present invention resides in a catheter having an outside diameter smaller than 1 mm which is composed of a resin inner tube, a reinforcing wire having two tiers with turns running around the inner tube obliquely to the axis and crossing each other, and a polyester resin film covering the reinforcing wire, said reinforcing wire being a low carbon duplex structure steel wire having a diameter smaller than 30 μm and a tensile strength higher than 300 kgf/mm².

The fourth aspect of the present invention resides in a catheter as defined in the third aspect, wherein the polyester resin film has a thickness smaller than 5 μm.

The fifth aspect of the present invention resides in a catheter as defined in the third or fourth aspect, wherein the resin inner tube is covered with a plurality of the reinforcing wires arranged in belt-like form and intertwined in reticular form.

The sixth aspect of the present invention resides in a catheter which comprises a resin inner tube, a reinforcing wire, a heater wire, a temperature sensor lead wire, and a resin coating film, said reinforcing wire, heater wire, and temperature sensor lead wire running around the inner tube in such a manner than they are electrically insulated from one another.

The seventh aspect of the present invention resides in a catheter as defined in the sixth aspect, wherein the temperature sensor is at the forward end of the catheter and the heater wire is positioned such that the forward end thereof is behind, or proximal to, the temperature sensor.

The reason for using a polyester resin for the coating film is that it can be formed into a very thin film which prevents the dissolution of metal and improves the resistance to corrosion by body fluids and medicine. The polyester resin coating film should preferably be formed by repeating the application of a resin solution, so that the resulting coating film has a high density.

For the effective coating of polyester resin on the low carbon duplex structure steel wire, it is desirable to form a nickel plating layer as the substrate. The nickel plating layer lowers the activity of the wire, improves the self-lubricity and corrosion resistance of the wire, and improves the adhesion to the polyester resin. Moreover, the nickel plating layer will exhibit the further improved adhesion to the polyester resin film if it is given strain hardening by plastic working.

According to the first and second aspects of the present invention, the catheter guide wire is composed of a core wire, a winding of a low carbon duplex structure steel wire having a diameter smaller than 30 μm and a tensile strength higher than 300 kgf/mm², and a polyester resin film covering the winding. The use of the low carbon duplex structure steel wire, unlike the conventional stainless steel wire, makes it possible to reduce the diameter of the guide wire, while retaining the characteristic properties required of the guide wire. Since the low carbon duplex structure steel wire is very thin, the resulting guide wire is still thinner than that of stainless steel wire even though its surface is coated with a polyester resin film. The polyester resin coating film is thin but protects the guide wire from corrosion even when it comes into direct contact with body fluids and medicine.

The catheter pertaining to the third aspect of the present invention employs the low carbon duplex structure steel wire for reinforcement. This reinforcement permits the wall thickness of the inserting part to be made thinner, without any adverse effect on the buckling resistance and torque transmission ability, and also permits the outside diameter to be reduced while securing the inside diameter required. The catheter pertaining to the fifth aspect of the present invention has improved flexibility.

According to the sixth aspect of the present invention, the catheter is composed of a resin inner tube, a reinforcing wire, a heater wire, a temperature sensor lead wire, and a resin coating film. Therefore, the catheter generates heat by itself to heat the medicine passing through it. The heating temperature of the medicine is detected by the temperature sensor and accurately controlled according to the intended use. This solves the problem of overheating or overcooling involved in the conventional method of heating and injecting the medicine separately, contributing to the reliability of diagnosis and medical treatment.

According to the seventh aspect of the present invention, the temperature sensor is at the forward end of the catheter and forward of the heater wire, so that the temperature sensor never detects the temperature of the heater wire. This contributes to the accurate temperature control.

EXAMPLES

Examples of the present invention will be described with reference to the accompanying drawings.

FIGS. 1 to 4 show the first embodiment of the catheter and catheter guide wire pertaining to the first to fourth aspects of the present invention.

Figure 4:
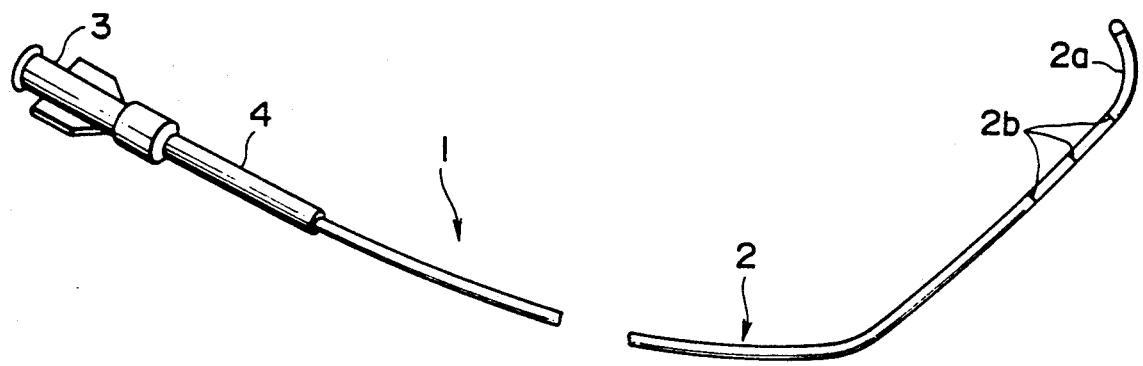
FIG. 4 is a perspective view showing the catheter in the first embodiment.

In FIG. 4, there is shown a catheter 1 for diagnosis and medical treatment, which is made up of a tubular inserting part 2 (1 meter long, 1 mm in outside diameter, and 0.6 mm in inside diameter), a manipulating part 3 for the blood extraction or medicine injection (fixedly connected to one end of the inserting part), and a guiding part 4 (rotatably fitted on the manipulating part). The inserting part 2 is formed slightly bent as the whole, with the forward end 2a thereof bent in "L". The forward end 2a has small holes 2b to facilitate the extraction of blood or body fluids or the injection of medicine.

Figure 3:
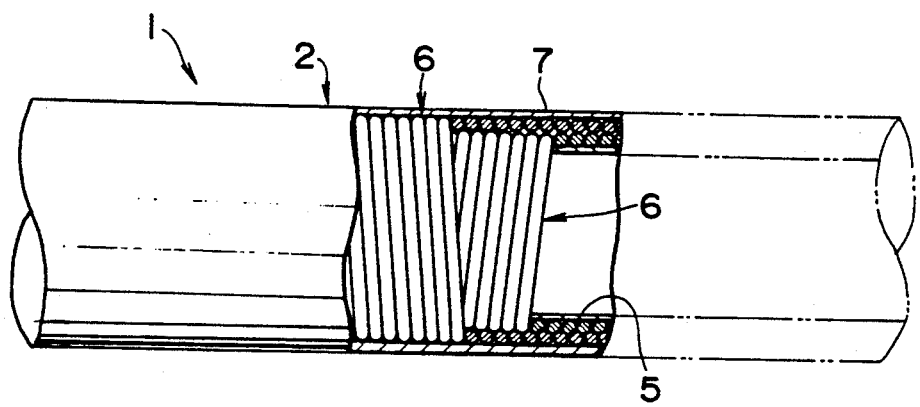
FIG. 3 is a partially sectional view illustrating the catheter in the first embodiment.

As FIG. 3 shows, the inserting part 2 is made up of an inner tube 5 of fluoroplastic, a layer of reinforcing wire 6, and a covering layer 7 of fluoroplastic. The reinforcing wire 6 is tightly running in two tiers around the inner tube 5, the turns of the tiers crossing each other and extending oblique to the axis. The covering layer 7 is formed from a heat-shrinkable tube of fluoroplastic slipped on the layer of reinforcing wire 6. Thus there is no gap between them.

FIG. 1 shows a catheter guide wire 10, which is 0.3 mm in outside diameter and approximately straight. It is inserted into the catheter 1 from the manipulating part 3 so as to keep approximately straight the inserting part 2 and forward end 2a of the catheter. The guide wire 10 is made up of a core 11 of stainless steel and a reinforcing wire 12 tightly wound double around the core in two tiers. The turns of the tiers of the reinforcing wire 12 run oblique to the axis of the core 11 and cross each other.

Figure 1B:
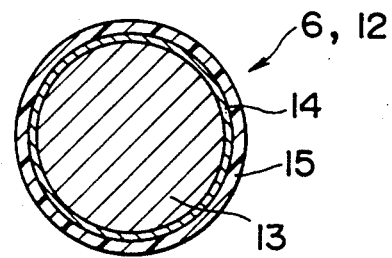

As FIG. 1(b) shows, the reinforcing wire 6 and 12 to constitute the guide wire 10 and catheter 1 is a low carbon duplex structure steel wire 13, 10-30 $\mu$m in diameter. It has the above-mentioned composition and is produced by the above-mentioned process. It has the fine metal structure composed of fibrous cells oriented in one direction, with the size of each cell being 5-100 Å and the distance between cells being 50-1000 Å. It has a tensile strength of 300-600 kgf/mm$^2$. It is covered with a nickel plating layer 14, about 1 $\mu$m thick, which is free from pin-holes owing to strain hardening induced by plastic working at the time of drawing.

The nickel plating layer 14 is coated with a polyester resin film 15, about 1-3 $\mu$m thick, which is formed by the repeated application of a polyester resin solution.

Figure 2:
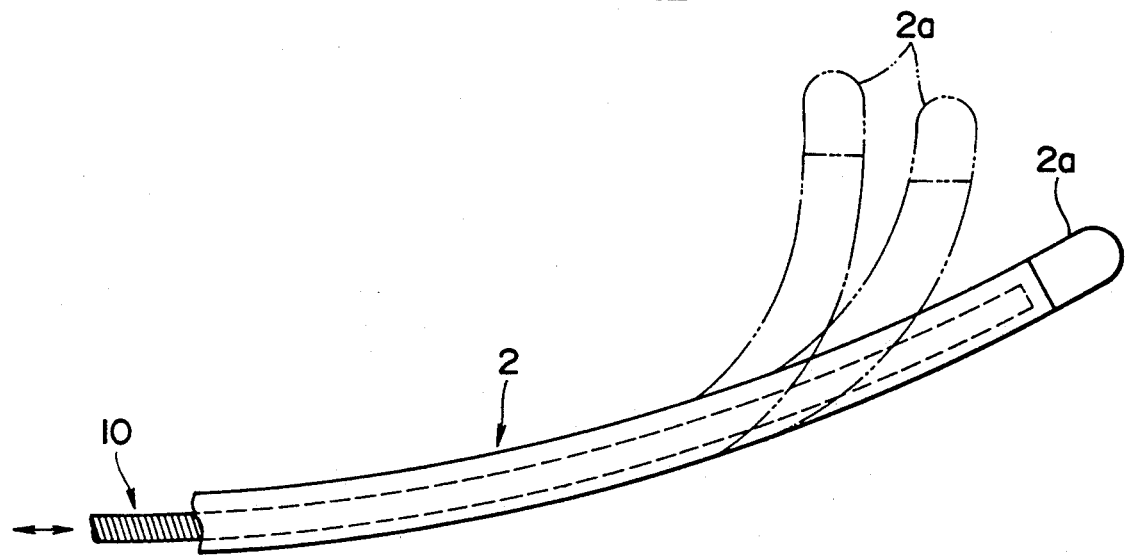
FIG. 2 is a diagram showing the catheter in the first embodiment, with the guide wire inserted thereinto.

The above-mentioned embodiment produces the following effects. When the catheter 1 is in use, the inserting part 2 is inserted into the coronary artery from the femoral artery for the administration of a radiopaque material through the small holes 2b therein. To insert the catheter 1 into the blood vessel, the guide wire 10 is inserted into the inserting part 2 so as to keep approximately straight the forward end 2a thereof, as shown in FIG. 2. When the forward end 2a reaches a bend of the blood vessel, the guide wire 10 is retracted to restore the forward end 2a to its original shape indicated by the chain line. In this way, the forward end 2a is directed to the target. The guide wire 10 is moved back and forth until the forward end 2a reaches the affected part.

According to this embodiment, the guide wire 10 is composed of the reinforcing wire 12 which is the low carbon duplex structure steel wire 13, the nickel plating layer 14, and the polyester resin coating film 15. The reinforcing wire 12 itself has a high tensile strength of 300 kgf/mm$^2$ and an extremely small diameter of 10-30 $\mu$m. Therefore, the guide wire can be made thin easily, unlike the conventional stainless steel wire, without any adverse effect on the retention of the catheter 1. The polyester resin thin film coating 15, which is easy to make, improves corrosion resistance and protects the guide wire from corrosion by medicine and blood. In addition, the nickel plating layer 14 improves the adhesion to the polyester resin film 15.

According to this embodiment, the low carbon duplex structure steel wire 13 is used as the reinforcing wire 6 of the catheter 1. This makes it possible to reduce the wall thickness of the inserting part 2 and hence to reduce the outside diameter while maintaining the desired inside diameter. The winding of the low carbon duplex structure steel wire 13 is flexible and yet retains its shape, improving the buckling resistance and torque transmitting ability.

In the first embodiment mentioned above, the reinforcing wire 6 for the catheter 1 is tightly wound double (in two tiers). However, the winding of the reinforcing wire is not limited to this structure.

Figure 5:
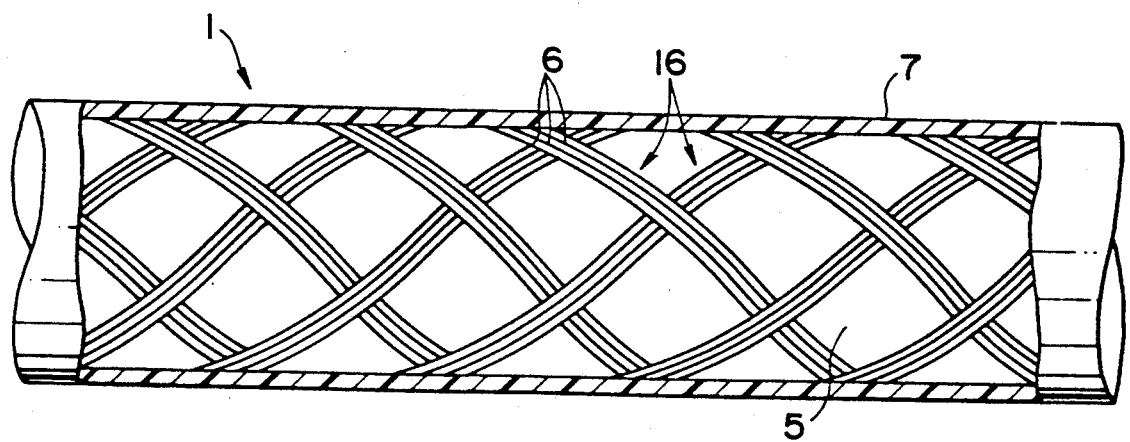
FIG. 5 is a partially sectional side view illustrating the catheter in the second embodiment pertaining to the third aspect of the present invention.

FIG. 5 shows the second embodiment pertaining to the fifth aspect of the present invention. In this embodiment, three reinforcing wires 6 (low carbon duplex structure steel wires) are arranged parallel in belt-like form 16 and they are intertwined in reticular form on the inner tube 5 of fluoroplastic. The reinforcing belts 16 are oblique to the axis and cross each other.

The catheter in the second embodiment exhibits the same characteristic properties as that in the first embodiment; moreover, it is more flexible.

The low carbon duplex structure steel wire used in the first and second embodiments was tested for corrosion resistance and tensile strength. The samples for the test were three low carbon duplex structure steel wires coated with polyester resin film, each having an outside diameter of 15, 26, and 30 $\mu$m (including the thickness of the resin coating film) and the resin coating film being 1 $\mu$m or 3 $\mu$m thick. The corrosion resistance was evaluated by measuring the area (in %) of the corrosion that occurred after the samples had been exposed to salt water spray for 2-8 hours, allowed to stand for 8 hours, and dried for 16 hours. For comparison, the same test as mentioned above was made with three samples: (1) a low carbon duplex structure steel wire, 35 $\mu$m in outside diameter, coated with a polyester film, 5 $\mu$m thick, (2) a SUS304 wire, 30 $\mu$m in diameter, and (3) a piano wire, 25,100 $\mu$m in diameter, without rust preventive treatment. The results are shown in Table 1.

TABLE 1

| | Tensile strength (kgf/mm$^2$) | Salt water spray test (Corroded area, %) | | | | |
|---|---|---|---|---|---|---|
| | | 2 hr | 4 hr | 6 hr | 8 hr | 8 hr + 16 hr dry |
| Embodiment | | | | | | |
| (a) 15 $\mu$m in dia. (1 $\mu$m coating) | 435 | 0% | 0% | 0% | 0% | 0% |
| (b) 26 $\mu$m in dia. (1 $\mu$m coating) | 400 | 0 | 0 | 0 | 0 | 0 |
| (c) 30 $\mu$m in dia. (3 $\mu$m coating) | 300 | 0 | 0 | 0 | 0 | 0 |
| Comparison | | | | | | |
| 35 $\mu$m in dia. (5 $\mu$m coating) Conventional material | 220 | 0 | 0 | 0 | 0 | 0 |
| SUS304 (30 $\mu$m in dia.) | 233 | 0 | 0 | 0 | 0 | 0 |
| Piano wire, 25 $\mu$m in dia. | — | 50 | 70 | 100* | — | — |
| Piano wire, 100 $\mu$m in dia. | — | 30 | 50 | 60 | 80 | — |

*broken

It is noted from Table 1 that in the case of conventional piano wire, the corroded area exceeded 50% (before breakage) 2-4 hours after salt water spray in the corrosion resistance test. By contrast, the low carbon duplex structure steel wire and SUS304 wire did not corrode at all even after drying that followed standing for 8 hours. It is also noted from Table 1 that the tensile strength of SUS304 wire is 233 kgf/mm$^2$, whereas that of three samples (a), (b), and (c) of the low carbon duplex structure steel wire is 435, 400, and 300 kgf/mm$^2$, respectively, in spite of their small diameter. The tensile strength of the low carbon duplex structure steel wire having an outside diameter of 35 $\mu$m is 220 kgf/mm$^2$, which is close to that of the stainless steel wire. This suggests that the resin coating film should be smaller than 3 μm in thickness. Incidentally, the tensile strength was obtained by dividing the load by the sectional area calculated from the outside diameter including the resin film thickness.

Figure 6:
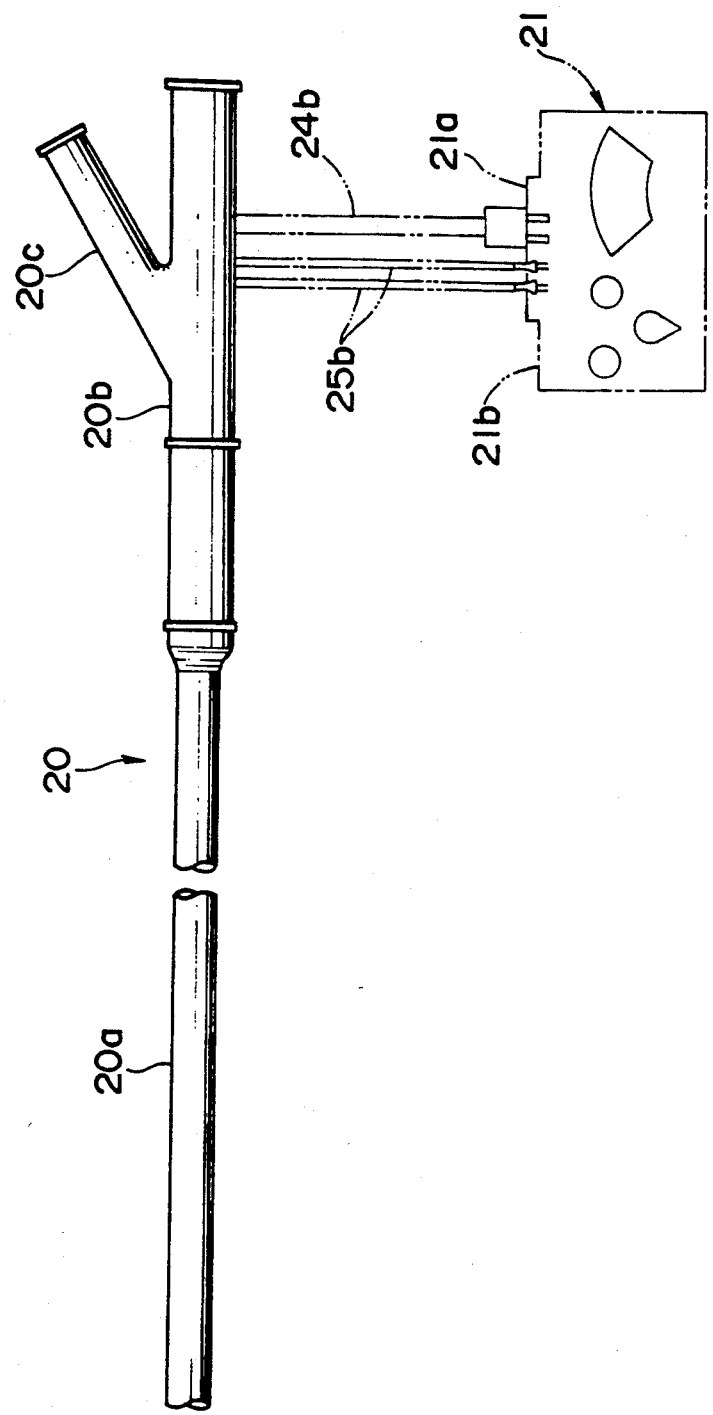
FIG. 6 is a schematic representation illustrating the catheter in the third embodiment pertaining to the fourth aspect of the present invention.
Figure 7:
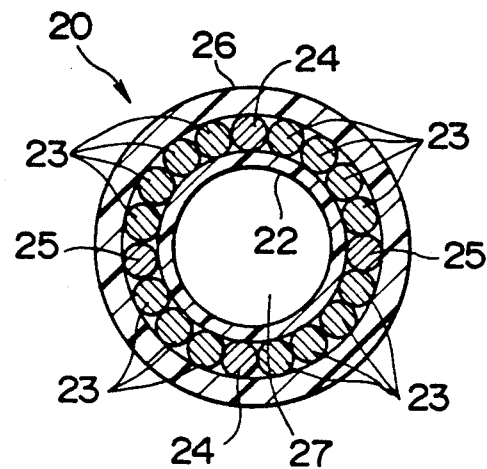
FIG. 7 is a sectional view of the catheter in the third embodiment.
Figure 8:
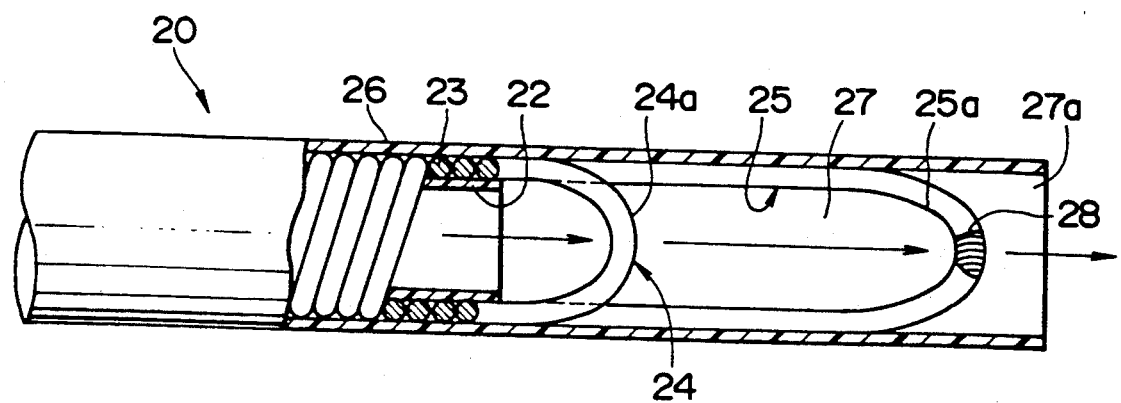
FIG. 8 is a sectional view showing the forward end of the catheter in the third embodiment.

FIGS. 6 and 7 show the catheter pertaining to the third embodiment of the present invention. The proximal end of the catheter 20 is composed of an inserting part 20a and a manipulating part 20b which are joined together, and a medicine injecting part 20c branches out from the manipulating part 20b. The manipulating part 20b is connected to a control unit 21 consisting mainly of a heating power supply 21a and a temperature controller 21b.

The catheter 20 is made up an inner tube 22 of fluoroplastic, a multiplicity of reinforcing wires 23 of low carbon duplex structure steel wire wound around the inner tube, a pair of heater wires 24, a lead wire 25 for thermocouple (heat sensor), a covering coating film 26 of fluoroplastic. A medicine is injected to the affected part through the passage 27 and the opening 27a thereof. Although not shown, the reinforcing wire 23, heater wire 24, and lead wire 25 are covered with an insulating film so that they are electrically insulated from one another.

The forward or distal end 24a of the heater wire 24 is at the end of the inner tube 22 and the rear end 24b of the heater wire 24 is connected to the heating power supply 21a in the control unit 21. The lead wires 25 are joined together at their forward ends 25a, and the joints functions as a temperature sensor 28. The temperature sensor 28 is beyond the forward end 24a of the heater wire 24, so that it does not detect the temperature of the heater itself. The rear end 25b of the lead wire 25 is connected to the temperature controller 21b.

When in use for the remedy of obstructive jaundice induced by liver cancer, for example, the catheter 20 in this embodiment is heated by energizing the heater wire 24 so that the anticancer drug for injection is heated. The temperature of the anticancer drug being injected is monitored by the temperature sensor 28. The monitored temperature is indicated on the temperature controller 21b, so that one can operate the power supply 21b to control the temperature of the drug as desired.

The catheter 20 in this embodiment, which has the reinforcing wire 23, heater wire 24, and lead wire 25, is capable of heating a medicine (such as anticancer drug) by heating itself, while maintaining the characteristic properties required of the catheter. In addition, it has a means to monitor the temperature of the medicine. Therefore, this catheter permits the accurate temperature control and the local heating of affected part. This alleviates the patient's pain, improves the remedial effect, and contributes to the reliability of remedy.

The catheter 20 can also be used for transfusion of blood in large quantities. In this case it is possible to perform transfusion while refrigerated blood is being heated. The reinforcing wire, heater wire, and lead wire may those which have a flat cross section, so that the catheter has a smaller outside diameter and improved elasticity.

EFFECTS OF THE INVENTION

The catheter guide wire pertaining to the first and second aspects of the present invention, which is made up of a core wire having a diameter smaller than 30 μm, a low carbon duplex structure steel wire having a tensile strength higher than 300 kgf/mm$^2$, and a polyester resin coating film having a thickness smaller than 5 μm, can be made thin easily without any adverse effect on the characteristic properties required of the guide wire. In addition, it has improved resistance to corrosion by body fluids and medicine.

The catheter pertaining to the third and fourth aspects of the present invention, which is reinforced with the above-mentioned low carbon duplex structure steel wire, exhibits improved buckling resistance and torque transmitting ability even though the wall thickness of the catheter is reduced. The catheter pertaining to the fifth aspect of the present invention, in which the reinforcing wires are wound in a reticular form, has improved flexibility.

The catheter pertaining to the sixth aspect of the present invention, which has the reinforcing wire, heater wire, and temperature sensor lead wire wound around the inner tube, can heat medicine or blood by heating itself with accurate temperature control. The catheter pertaining to the seventh aspect of the present invention is improved in temperature control accuracy because the temperature sensor never monitors the temperature of the heater wire itself.

What is claimed is:

1. A guide wire to keep a tubular catheter approximately straight, said guide wire comprising a core wire, a winding of a low carbon duplex structure steel wire having a diameter smaller than 30 μm and a tensile strength higher than 300 kgf/mm$^2$, said winding having two tiers and covering the core wire such that the low carbon duplex structure steel wire runs obliquely to the axis of the core wire and the turns of the tiers cross each other, and a polyester resin film covering the low carbon duplex structure steel wire about substantially the entire circumference of the wire.

2. A guide wire as defined in claim 1, wherein the polyester resin film has a thickness smaller than 5 um.

3. The guide wire of claim 1, including a nickel layer between said low carbon duplex structure steel wire and said polyester resin film.

4. The guide wire of claim 3, wherein said nickel layer is about 1 μm thick.

* * * * *